(12) United States Patent
Ohno (10) Patent No.: US 8,758,574 B2
(45) Date of Patent: Jun. 24, 2014

(54) RUTILE TITANIUM DIOXIDE NANOPARTICLES EACH HAVING NOVEL EXPOSED CRYSTAL FACE AND METHOD FOR PRODUCING SAME

(75) Inventor: Teruhisa Ohno, Kitakyushu (JP)

(73) Assignee: Daicel Corporation, Osaka (JP)

( * ) Notice: Subject to any disclaimer, the term of this patent is extended or adjusted under 35 U.S.C. 154(b) by 40 days.

(21) Appl. No.: 13/389,097

(22) PCT Filed: Jul. 13, 2010

(86) PCT No.: PCT/JP2010/062131
§ 371 (c)(1),
(2), (4) Date: Feb. 6, 2012

(87) PCT Pub. No.: WO2011/016329
PCT Pub. Date: Feb. 10, 2011

(65) Prior Publication Data
US 2012/0132515 A1    May 31, 2012

(30) Foreign Application Priority Data
Aug. 5, 2009  (JP) .................................. 2009-182563

(51) Int. Cl.
    C07F 1/00     (2006.01)
    C07F 3/00     (2006.01)
    C07F 5/00     (2006.01)
    C01G 23/047   (2006.01)
    B01J 23/00    (2006.01)

(52) U.S. Cl.
    USPC ......... 204/157.6; 423/610; 502/350; 977/773

(58) Field of Classification Search
    USPC .................. 423/610–616; 977/773, 775, 776; 502/350; 204/157.6
    See application file for complete search history.

(56) References Cited

U.S. PATENT DOCUMENTS 7,303,723 B2 * 12/2007 Akbar et al. ............... 264/677
(Continued)

FOREIGN PATENT DOCUMENTS

JP    2004359472 A  * 12/2004
JP    2005-298296 A    10/2005
(Continued)

OTHER PUBLICATIONS

Chen et al., "Titanium Dioxide Nanomaterials: Synthesis, Properties, Modifications, and Applications," Chem. Rev. 2007, 107, 2891-2959.*

(Continued)

*Primary Examiner* — Anthony J Zimmer
(74) *Attorney, Agent, or Firm* — Birch, Stewart, Kolasch & Birch, LLP (57) ABSTRACT

Provided are: novel rutile titanium dioxide nanoparticles each having a high photocatalytic activity; a photocatalyst including the rutile titanium dioxide nanoparticles; and a method for oxidizing an organic compound using the photocatalyst. The rutile titanium dioxide nanoparticles each have an exposed crystal face (001). The rutile titanium oxide nanoparticles may be produced by subjecting a titanium compound to a hydrothermal treatment in an aqueous medium in the presence of a hydrophilic polymer. A polyvinylpyrrolidone, for example, is used as the hydrophilic polymer. An organic compound having an oxidizable moiety can be oxidized with molecular oxygen or a peroxide under photoirradiation in the presence of the photocatalyst including the rutile titanium oxide nanoparticles.

6 Claims, 7 Drawing Sheets

(56) References Cited

U.S. PATENT DOCUMENTS

| | | | |
|---|---|---|---|
| 7,521,394 B2* | 4/2009 | Xie et al. | 502/350 |
| 2004/0126624 A1* | 7/2004 | Akbar et al. | 428/701 |
| 2007/0202334 A1* | 8/2007 | Xie et al. | 428/402 |
| 2008/0223713 A1* | 9/2008 | Xu et al. | 204/157.15 |
| 2009/0005238 A1 | 1/2009 | Falaras | |
| 2010/0139747 A1* | 6/2010 | Feng et al. | 136/255 |
| 2012/0028791 A1* | 2/2012 | Osterlund et al. | 502/171 |

FOREIGN PATENT DOCUMENTS

| | | |
|---|---|---|
| JP | 2006-224084 A | 8/2006 |
| JP | 2006-225623 A | 8/2006 |
| JP | 2008-195551 A | 8/2008 |
| JP | 2009-519889 A | 5/2009 |

OTHER PUBLICATIONS

Hengbo Yin, "Morphology and Photocatalysis of TiO2 Prepared by Hydrothermal Synthesis-Rutile Type", 79th Annual Meeting of Chemical Society of Japan in Spring (2001) Koen Yokoshu I, Mar. 15, 2001, p. 370, lower left part.

Hironori Shimoita et al., "Suinetsuho ni yoru Rutile-gata Sanka Titanium Nano-ryushi no Gosei to Hikari Shokubai Kino Hyoka", The Ceramic Society of Japan 2008 Nen Nenkai Koen Yokoshu, Mar. 20, 2008, p. 217.

International Search Report issues PCT/JP2010/062131 dated Sep. 28, 2010.

Lei Yang et al., "Suiyosei Polymer Kyozonka ni Okeru Rutile-gata Nisanka Titanium Biryushi no Sentakuteki Chosei", Abstracts, Annual Meeting of The Society of Polymer Science, Japan, May 10, 2007, vol. 56, No. 1, p. 1137.

* cited by examiner

RUTILE TITANIUM DIOXIDE NANOPARTICLES EACH HAVING NOVEL EXPOSED CRYSTAL FACE AND METHOD FOR PRODUCING SAME

TECHNICAL FIELD

The present invention relates to rutile titanium dioxide nanoparticles that are useful as photocatalysts and oxidation catalysts; production method thereof; a photocatalyst including the rutile titanium dioxide nanoparticles; and a method for oxidizing an organic compound using the photocatalyst.

BACKGROUND ART

A photocatalytic reaction is a reaction in which excited electrons and holes (positive holes: holes) out of which the electrons have gone are generated upon irradiation of a solid compound having a photocatalytic activity with an ultraviolet ray, whereby a reactant is oxidized or reduced because the excited electrons each have a reducing action, and the holes each have a strong oxidizing action. Titanium dioxide is known as a typical solid compound having a photocatalytic activity. Titanium dioxide can exhibit a strong oxidizing action upon absorption of an ultraviolet ray and is thereby applied in a wide variety of applications such as air purification, water purification, pollution control, deodorization, antimicrobe, prevention of hospital infection, and demisting.

Rutile and anatase crystal forms are known as major crystal forms of titanium dioxide. These crystalline titanium dioxides display higher chemical stability and larger refractive indices than those of amorphous titanium dioxide (amorphous). In addition, the crystalline titanium dioxides are easily controllable on shape, size, and degree of crystallinity, of crystals.

It has been also known that titanium dioxide particles each having a high degree of crystallinity can exhibit a superior photocatalytic activity to that of titanium dioxide powders each having a low degree of crystallinity; and that, with an increasing crystal size, the titanium dioxide particles exhibit more satisfactory photocatalytic activity.

Patent Literature (PTL) 1 describes a method for preparing a titanium dioxide crystal having a novel exposed crystal face being developed by subjecting titanium dioxide to a treatment with a basic hydrogen peroxide solution, a treatment with sulfuric acid, or a treatment with hydrofluoric acid; and mentions that a photocatalyst including the prepared titanium dioxide having a newly exposed, novel exposed crystal face has a high oxidative catalytic capability. The literature discloses, as examples of the titanium dioxide having a novel exposed crystal face, (1) a titanium dioxide crystal obtained from rutile titanium dioxide and having a newly exposed (novel exposed) (121) face; (2) a titanium dioxide crystal obtained from rutile titanium dioxide and having newly exposed (001), (121), (021), and (010) faces; (3) a titanium dioxide crystal obtained from rutile titanium dioxide and having a newly exposed (021) face; (4) a titanium dioxide crystal obtained from anatase titanium dioxide and having a newly exposed (120) face; (5) a titanium dioxide crystal obtained from anatase titanium dioxide and having a newly exposed (122) face; and (6) a titanium dioxide crystal obtained from anatase titanium dioxide and having a newly exposed (112) face.

However, such titanium dioxide catalysts having conventional crystal forms do not sufficiently exhibit catalytic actions in some applications, and demands have been made to provide a titanium dioxide photocatalyst having a higher catalytic activity.

CITATION LIST

Patent Literature

PTL 1: Japanese Unexamined Patent Application Publication (JP-A) No. 2005-298296

SUMMARY OF INVENTION

Technical Problem

Accordingly, an object of the present invention is to provide: novel rutile titanium dioxide nanoparticles each having a high photocatalytic activity; a photocatalyst including the rutile titanium dioxide nanoparticles; and a method for oxidizing an organic compound using the photocatalyst.

Another object of the present invention is to provide: a photocatalyst including novel rutile titanium dioxide nanoparticles that are capable of efficiently oxidizing an organic substance; and a method for oxidizing an organic compound using the photocatalyst.

Solution to Problem

After intensive investigations to achieve the objects, the present inventors have found that it is important for increase in photocatalytic activity to separate electrons from holes each of which induces a photocatalytic reaction, because the electrons and holes, if approach to each other, are liable to recombine with each other; that the exposing of a novel exposed crystal face (001) in a titanium dioxide crystal facilitates the separation of electrons from holes; that rutile titanium dioxide nanoparticles each having the exposed crystal face (001) are obtained by subjecting a titanium compound to a hydrothermal treatment in an aqueous medium in the presence of a hydrophilic polymer; and that a photocatalyst including the rutile titanium dioxide nanoparticles each having the exposed crystal face (001) has high oxidative catalytic performance. The present invention has been made based on these findings.

Specifically, the present invention provides a rutile titanium dioxide nanoparticle having an exposed crystal face (001).

The present invention provides, in another aspect, a method for producing rutile titanium dioxide nanoparticles. The method includes the step of subjecting a titanium compound to a hydrothermal treatment in the presence of a hydrophilic polymer in an aqueous medium to yield rutile titanium dioxide nanoparticles each having an exposed crystal face (001).

The hydrophilic polymer is preferably a polyvinylpyrrolidone.

The present invention provides, in yet another aspect, a photocatalyst including rutile titanium dioxide nanoparticles each having an exposed crystal face (001).

In addition, the present invention provides a method for oxidizing an organic compound. The method includes the step of oxidizing an organic compound having an oxidizable moiety with molecular oxygen or a peroxide under photoirradiation in the presence of a photocatalyst including rutile titanium dioxide nanoparticles each having an exposed crystal face (001).

Advantageous Effects of Invention

A rod-like crystal of rutile titanium dioxide has (110) and (111) faces, in which the (110) face acts as a reduction site, and the (111) face acts as an oxidation site. The rutile titanium dioxide nanoparticles according to the present invention each have a novel exposed crystal face (001) in addition to the exposed (110) and (111) crystal faces, in which the (110) face acts as a reduction site, and the (001) face and the (111) face act as oxidation sites. Accordingly, excited electrons and activated holes generated upon irradiation with an ultraviolet ray can be fully separated from each other and protected from recombination. The rutile titanium dioxide nanoparticles can therefore exhibit a strong oxidizing action. The rutile titanium dioxide nanoparticles according to the present invention, when used as a photocatalyst, enable efficient oxidation of an organic substance and are useful for the purposes typically of air purification, deodorization, water purification, antimicrobe, and antifouling.

DESCRIPTION OF EMBODIMENTS

Embodiments of the present invention will be illustrated in detail below with reference to the drawings according to necessity.

The rutile titanium dioxide nanoparticles according to the present invention each have a novel exposed crystal face (001).

Figure 1:
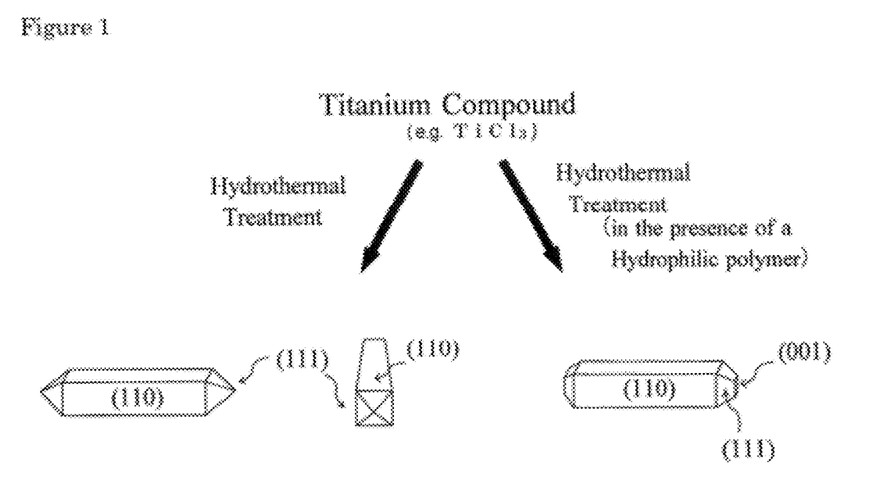
FIG. 1 is a diagram schematically illustrating a crystal obtained by subjecting a Titanium Compound such as $TiCl_3$ to a Hydrothermal Treatment in the absence of a polyvinylpyrrolidone (PVP); and a crystal obtained by subjecting a titanium compound to a hydrothermal treatment in the presence of a PVP (in the presence of a Hydrophiric polymer).

The rutile titanium dioxide nanoparticles each having a novel exposed crystal face (001) may be prepared by subjecting a titanium compound to a hydrothermal treatment in the presence of a hydrophilic polymer in an aqueous medium. A titanium compound, when hydrothermally treated in an aqueous medium, generally gives a rod-like crystal of rutile titanium dioxide having the (110) and (111) faces. However, a titanium compound, when hydrothermally treated in an aqueous medium in the presence of a hydrophilic polymer, gives a rod-like crystal of rutile titanium dioxide having a novel exposed crystal face (001) (see FIG. 1).

Exemplary titanium compounds include titanium trichloride, titanium tetrachloride, titanium tetrabromide, titanium sulfate, titanium nitrate, titanium alkoxides, and titanium peroxide. Titanium trichloride and/or titanium tetrachloride is preferably used in the present invention from the points of reactivity and abundance of chloride ions in the atmosphere (in the air) in a reaction system as an open system.

Upon the synthesis of the colloidal nanoparticles, the hydrophilic polymer acts as a steric stabilizer or capping agent to thereby prevent the aggregation of the product. Exemplary hydrophilic polymers include polyalkylene oxides such as polyethylene oxides (PEOs) and polypropylene oxides; as well as polyvinylpyrrolidones (PVPs), poly(vinyl alcohol)s, poly(vinyl acetate)s (PVAs), poly(hydroxyalkyl acrylate)s, polystyrenesulfonates, and mixtures or copolymers of them.

Among them, PVPs and PVAs are preferred as the hydrophilic polymer for use in the present invention, of which PVPs are more preferred, because they are chemically stable, have no toxicity, display satisfactory solubility in a number of polar solvents, and are adsorbed by the (111) face of the rutile titanium dioxide nanoparticles to thereby control the shape of the rutile titanium dioxide nanoparticles.

A PVP for use herein has an average molecular weight of typically from about 10000 to about 100000, and preferably from about 30000 to about 50000. The PVP, if having an average molecular weight of less than 10000, may be liable to exhibit insufficient functions of controlling the shape of the rutile titanium dioxide nanoparticles as being adsorbed by the specific surface of the nanoparticles, and of preventing the aggregation of the product. In contrast, the PVP, if having an average molecular weight of more than 100000, may have an excessively high viscosity to cause insufficient workability, and the polymer (PVP) itself may have insufficient dispersibility. Thus, the PVP may be liable to have an insufficient capability of controlling the shape of the rutile titanium dioxide nanoparticles due to lack of satisfactory interaction with the titanium oxide precursor.

Exemplary commercial products usable in the present invention as the PVP include products under the trade name "PVP-K30" (average molecular weight: 40000) and the trade name "PVP-K25" (average molecular weight: 24000).

The photocatalytic activity of the rutile titanium dioxide nanoparticles is significantly affected by the crystal structure of the particles. This is because the degree of easiness of recombination between excited electrons and holes, which are generated upon the irradiation with an ultraviolet ray, varies depending on the crystal structure of the particles. A hydrophilic polymer such as a PVP is more liable to be adsorbed, of the crystal face (111) and crystal face (110) of the rutile titanium dioxide nanoparticles, by the crystal face (111) and act to erode a portion corresponding to an edge or apex to expose a novel exposed crystal face (001). Thus, by regulating the concentration of the hydrophilic polymer, the shape of the novel exposed crystal face (001) can be controlled. Accordingly, the novel exposed crystal face (001) can be exposed and can have a larger area as depending on the concentration of the hydrophilic polymer. In contrast, the area of the crystal face (111) decreases inversely proportionally to an increasing concentration of the hydrophilic polymer.

The concentration of the hydrophilic polymer such as a PVP herein is typically from 0.05 to 1.0 mM, preferably from about 0.2 to about 0.5 mM, and particularly preferably from 0.2 to 0.4 mM. The hydrophilic polymer, if used in an excessively high concentration, may excessively erode the crystal face (111) and cause the crystal face (111) to be excessively small. This may reduce the separation capability between electrons and holes and may cause them to be recombined with each other easily, and the resulting rutile titanium dioxide nanoparticles are liable to have an insufficient photocatalytic activity. In contrast, the hydrophilic polymer, if used in an excessively high concentration, may not satisfactorily form such a sufficient novel exposed face (001) as to separate electrons and holes from each other, and this tends to impede the improvement of the photocatalytic activity.

The aqueous medium for use in the present invention upon the hydrothermal treatment is water or a mixture of water and a water-miscible organic solvent. Exemplary water-miscible organic solvents include alcohols such as methanol and ethanol; ethers such as ethylene glycol dimethyl ether; ketones such as acetone; nitriles such as acetonitrile; and carboxylic acids such as acetic acid. The ratio (by weight) of water to a water-miscible organic solvent, when used as a mixture of them, is from about 10:90 to about 99.9:0.01, and preferably from about 50:50 to about 99:1. The aqueous medium is used in an amount of generally from about 0.0001 to about 0.1 part by weight, and preferably from about 0.001 to about 0.01 part by weight, per 1 part by weight of the titanium compound.

The aqueous medium for use in the present invention preferably further contains a halide. Exemplary halides include alkali metal halides such as sodium chloride, potassium chloride, lithium chloride, sodium bromide, potassium bromide, and lithium bromide. Among them, alkali metal halides are preferred, of which sodium chloride is particularly preferred. The addition of a halide to the aqueous medium enables the control of crystallinity, particle size, and surface area of the rutile titanium dioxide nanoparticles. There is a tendency that the particle size and crystallinity increase and the surface area decrease with an increasing amount of the halide. The amount of the halide for use herein is typically from about 0.5 to about 10 M, and preferably from about 1 to about 6 M.

The treatment temperature in the hydrothermal treatment may be chosen as appropriate in consideration of the reaction rate and reaction selectivity and is generally from about 100° C. to about 200° C., and the reaction time is from about 3 to about 24 hours. The pressure in the hydrothermal treatment is generally from about normal atmospheric pressure to about 0.3 MPa (gauge pressure), but is not limited to this range.

The rutile titanium dioxide nanoparticles according to the present invention having a novel exposed crystal face (001) as developed (exposed) are usable as photocatalysts typically in various chemical reactions (e.g., oxidation reactions and decomposition reactions of harmful substances) and sterilization.

The method for oxidizing an organic compound according to the present invention includes the step of oxidizing an organic compound having an oxidizable moiety with molecular oxygen or a peroxide under photoirradiation in the presence of a photocatalyst including the rutile titanium dioxide nanoparticles each having an exposed crystal face (001).

The organic compound is not limited, as long as being an organic compound having at least one oxidizable moiety. Exemplary organic compounds each having an oxidizable moiety include (A1) heteroatom-containing compounds each having a carbon-hydrogen bond at the adjacent position to the heteroatom; (A2) compounds each having a carbon-heteroatom double bond; (A3) compounds each having a methine carbon atom; (A4) compounds each having a carbon-hydrogen bond at the adjacent position to an unsaturated bond; (A5) non-aromatic cyclic hydrocarbons; (A6) conjugated compounds; (A7) amines; (A8) aromatic compounds; (A9) linear alkanes; and (A10) olefins.

Examples of the heteroatom-containing compounds (A1) each having a carbon-hydrogen bond at the adjacent position to the heteroatom include (A1-1) primary or secondary alcohols, and primary or secondary thiols; (A1-2) ethers each having a carbon-hydrogen bond at the adjacent position to oxygen atom, and sulfides each having a carbon-hydrogen bond at the adjacent position to sulfur atom; (A1-3) acetals (including hemiacetals) each having a carbon-hydrogen bond at the adjacent position to oxygen atom, and thioacetals (including thiohemiacetals) each having a carbon-hydrogen bond at the adjacent position to sulfur atom.

Examples of the compounds (A2) each having a carbon-heteroatom double bond include (A2-1) carbonyl-containing compounds, (A2-2) thiocarbonyl-containing compounds, and (A2-3) imines.

The compounds (A3) each having a methine carbon atom include (A3-1) cyclic compounds each containing a methine group (i.e., methine carbon-hydrogen bond) as a ring-constitutional unit; and (A3-2) chain compounds each having a methine carbon atom.

Examples of the compounds (A4) each having a carbon-hydrogen bond at the adjacent position to an unsaturated bond include (A4-1) aromatic compounds each having methyl group or methylene group at the adjacent position to the aromatic ring (so-called benzyl position); and (A4-2) non-aromatic compounds each having methyl group or methylene group at the adjacent position to an unsaturated bond (e.g., carbon-carbon unsaturated bond or carbon-oxygen double bond).

The non-aromatic cyclic hydrocarbons (A5) include (A5-1) cycloalkanes and (A5-2) cycloalkenes.

Examples of the conjugated compounds (A6) include conjugated dienes (A6-1); α, β-unsaturated nitriles (A6-2); and α, β-unsaturated carboxylic acids or derivatives (e.g., esters, amides, and acid anhydrides) of them (A6-3).

The amines (A7) include primary or secondary amines.

Examples of the aromatic hydrocarbons (A8) include aromatic compounds having at least one benzene ring, of which preferred are fused polycyclic aromatic compounds in which at least two or more (e.g., two to ten) benzene rings are fused.

Examples of the linear alkanes (A9) include linear alkanes each having 1 to about 30 carbon atoms (of which those each having 1 to about 20 carbon atoms are preferred).

The olefins (A10) may be whichever of a-olefins and internal olefins, each of which may have one or more substituents (e.g., the aforementioned substituents such as hydroxyl group and acyloxy groups). The olefins (A10) also include dienes and other olefins each having two or more carbon-carbon double bonds.

Each of different organic compounds each having an oxidizable moiety may be used alone or in combination, and in the latter case, the compounds used in combination may belong to the same or different categories.

The rutile titanium dioxide nanoparticles may be used in the oxidation method according to the present invention in an amount of typically from about 1 to about 10000 parts by weight, preferably from about 10 to about 5000 parts by weight, and furthermore preferably from about 50 to about 2000 parts by weight, per 100 parts by weight of the organic compound used as a substrate.

According to the method of the present invention, the organic compound as a substrate is oxidized with molecular oxygen and/or a peroxide under photoirradiation. As light to be applied, an ultraviolet ray of less than 380 nm is generally used, but visible light having a long wavelength of, for example, 380 nm or more and about 650 nm or less may be used in some types of the titanium dioxide.

The molecular oxygen for use herein may be pure oxygen; or oxygen diluted with an inert gas such as nitrogen, helium, argon, or carbon dioxide gas; or air. The molecular oxygen is used in an amount of typically 0.5 mole or more, and preferably 1 mole or more, per 1 mole of the organic compound used as a substrate. The molecular oxygen is often used in excess moles to the organic compound.

The peroxide is not limited and may be any of, for example, peroxides and hydroperoxides. Typical peroxides include hydrogen peroxide, cumene hydroperoxide, t-butyl hydroperoxide, triphenylmethyl hydroperoxide, t-butyl peroxide, and benzoyl peroxide. The hydrogen peroxide may be a pure hydrogen peroxide but is generally used in a form as diluted with a suitable solvent such as water (e.g., a 30 percent by weight hydrogen peroxide solution). The peroxide is used in an amount of typically from about 0.1 to about 5 moles, and preferably from about 0.3 to about 1.5 moles, per 1 mole of the organic compound used as a substrate.

According to the present invention, only one of molecular oxygen and a peroxide may be used, but the combination use of the molecular oxygen and peroxide may significantly increase the reaction rate in some cases.

The reaction allows organic compounds to give, for example, corresponding oxidative-cleavage products (e.g., aldehyde compounds), quinones, hydroperoxides, hydroxyl-containing compounds, carbonyl compounds, carboxylic acids and other oxygen-containing compounds. Typically, an alcohol gives, for example, a corresponding carbonyl compound (ketone and/or aldehyde) and a carboxylic acid; and an aldehyde gives, for example, a corresponding carboxylic acid. Adamantane gives, for example, 1-adamantanol, 2-adamantanol, and 2-adamantanone. The oxidation reaction, when further proceeds, decomposes an organic compound ultimately to carbon dioxide and water.

Such a reaction product may be separated and purified by a separation process such as filtration, concentration, distillation, extraction, crystallization, recrystallization, or column chromatography, or a separation process as a combination of these processes. In addition, the photocatalyst including the titanium dioxide nanoparticles can be easily separated by filtration, and the separated catalyst may be recycled, where necessary after being subjected to a treatment such as washing.

EXAMPLES

The present invention will be illustrated in further detail with reference to several working examples below. It should be noted, however, that these examples are never construed to limit the scope of the present invention.

Examples 1

An aqueous solution (50 mL) containing $TiCl_3$ (0.15 M), NaCl (5 M), and a PVP (trade name "PVP-K30", molecular weight: 40000, 0.25 mM) was charged in an autoclave coated with Teflon (registered trademark), followed by a hydrothermal treatment in an oven at 180° C. for 10 hours. The resulting reaction mixture was centrifugally separated, rinsed with deionized water, and dried in a vacuum drier (vacuum oven).

An organic compound remained or adsorbed on the surface was removed through ultraviolet irradiation for 24 hours using a lighting system with a 500-W super-high-pressure mercury lamp (trade name "SX-UI501U0", supplied by Ushio Inc.). Next, the residual article was dried at 60° C. under reduced pressure for 6 hours and thereby yielded $TiO_2$ (SH5-0.25PVP).

Examples 2 to 4

A series of $TiO_2$ (SH5-0.1PVP, SH5-0.4PVP, and SH5-0.5PVP) was obtained by the procedure of Example 1, except for changing the PVP concentration from 0.25 mM to 0.1 mM (Example 2), 0.4 mM (Example 3), and 0.5 mM (Example 4), respectively.

Comparative Example 1

$TiO_2$ (SH5-0PVP) was obtained by the procedure of Example 1, except for not using PVP.

The $TiO_2$ samples obtained in the examples and comparative example were assessed by the following methods. As a control, $TiO_2$ (trade name "MT-600B", supplied by Tayca Corporation, specific surface area: 25 to 35 $m^2/g$) was used.

<Morphological Assessment 1>

To an aqueous solution (2 g/L) of $TiO_2$ (SH5-0.25PVP) obtained in Example 1 were added 2-propanol (0.52 M) and $H_2PtCl_6 \cdot 6H_2O$ (1 mM) and thereby yielded a suspension. The resulting suspension, from which nitrogen gas was completely removed, was then irradiated with an ultraviolet ray (1 $mW/cm^2$) for 24 hours using a lighting system with a 500-W super-high-pressure mercury lamp (trade name "SX-UI501HQ", supplied by Ushio Inc.). The ultraviolet irradiation changed the color of the $TiO_2$ powder from white to gray. This indicates that Pt was photodeposited thereon. The resulting suspension was centrifugally separated, rinsed with distilled water, dried at 70° C. under reduced pressure for 3 hours, and thereby yielded a Pt-supporting $TiO_2$ powder.

An aqueous solution (2 g/L) containing the obtained Pt-supporting $TiO_2$ was combined with $Pb(NO_3)_2$ (0.1 M), further combined with nitric acid to adjust a pH to 1.0, and irradiated with an ultraviolet ray for 24 hours (0.1 $W/cm^2$) using a 500-W mercury lamp, and thereby yielded a $TiO_2$ supporting Pt and $PbO_2$ on the surface. The ultraviolet irradiation changed the color of the powder from gray to brown. This demonstrates that $Pb^{2+}$ ions were oxidized by the action of $TiO_2$ and precipitated as $PbO_2$.

Figure 2:
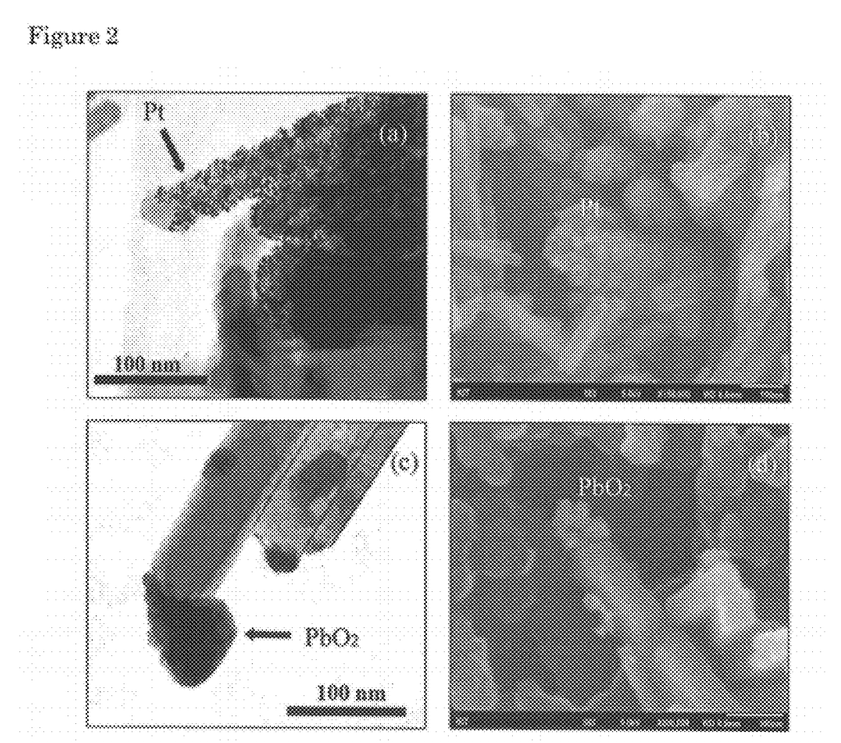
FIG. 2 depicts a transmission electron micrograph (TEM) (a) and a scanning electron micrograph (SEM) (b), respectively, of rutile titanium dioxide nanoparticles on which Pt is photodeposited; and a transmission electron micrograph (TEM) (c) and a scanning electron micrograph (SEM) (d), respectively, of rutile titanium dioxide nanoparticles on which Pt and $PbO_2$ are photodeposited.

The $TiO_2$ supporting Pt and $PbO_2$ on the surface was identified using a scanning electron microscope (SEM), an energy dispersive X-ray fluorescence analyzer (EDX) and a transmission electron microscope (TEM). The results demonstrated that, of the $TiO_2$, Pt was supported on the (110) face, whereas $PbO_2$ was supported on the (001) face and the (111) face. This demonstrates that an oxidation reaction occurs on the novel exposed face (001) and the (111) face, whereas a reduction reaction occurs on the (110) face in the rutile $TiO_2$ and that the oxidation reaction and the reduction reaction are thoroughly separated from each other (FIG. 2).

<Morphological Assessment 2>

Figure 3:
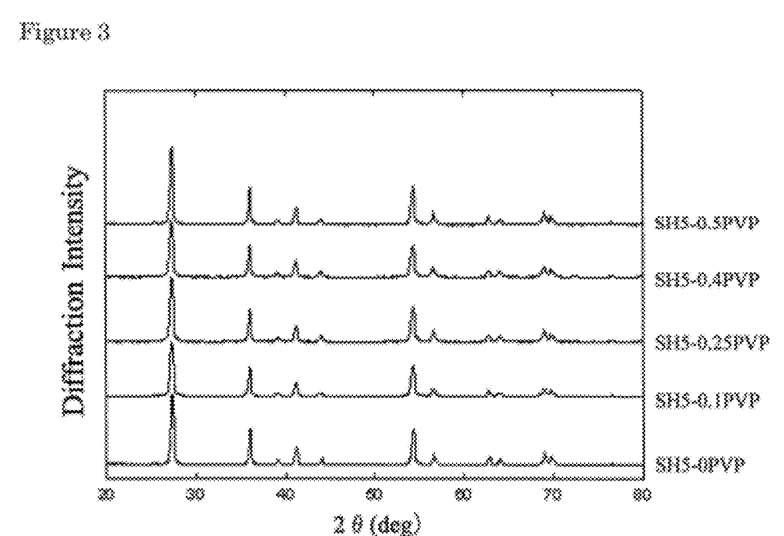
FIG. 3 depicts X-ray diffraction patterns of rutile titanium dioxide nanoparticles prepared at different PVP concentration varying from 0 to 0.5 mM in examples and comparative example, with the ordinate indicating the diffraction intensity (Diffraction Intensity) and the abscissa indicating the diffraction angle (2θ).
Figure 4:
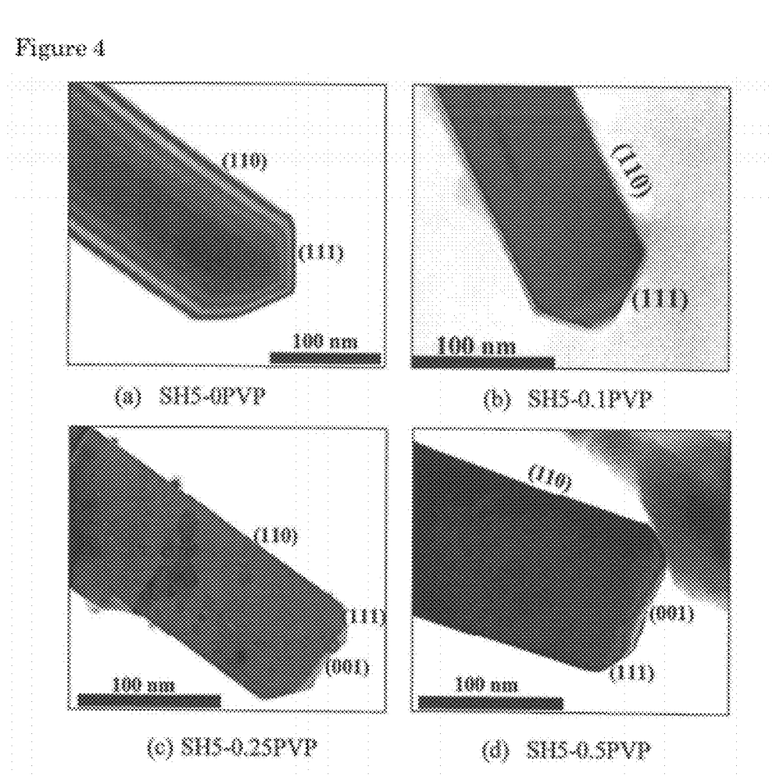
FIG. 4 depicts transmission electron micrographs of rutile titanium dioxide nanoparticles synthetically prepared at different PVP concentrations [(a) SH5-0PVP, (b) SH5-0.10PVP, (c) SH5-0.25PVP, and (d) SH5-0.5PVP]in the examples and comparative example.
Figure 5:
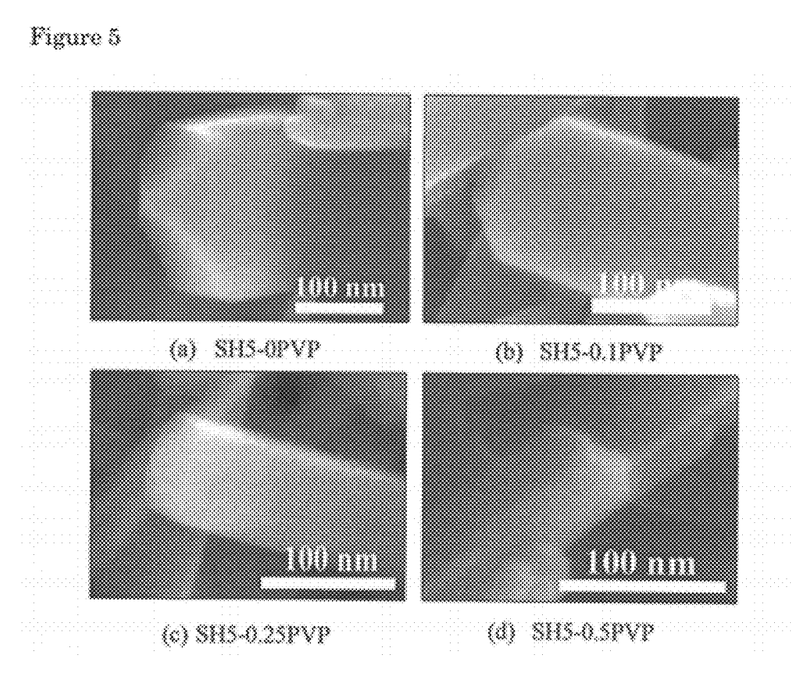
FIG. 5 depicts scanning electron micrographs of rutile titanium dioxide nanoparticles synthetically prepared at different PVP concentrations [(a) SH5-0PVP, (b) SH5-0.10PVP, (c) SH5-0.25PVP, and (d) SH5-0.5PVP] in the examples and comparative example.

Phase identification of the $TiO_2$ samples obtained in Examples 1 to 4 and Comparative Example 1 was performed using an XRD (powder X-ray diffractometer, trade name "JDX3500", supplied by JEOL, Cu-Kα, λ=1.5405 angstroms). Microstructures of them were determined using a transmission electron microscope (TEM, trade name "H-9000NAR", supplied by Hitachi) and a field emission scanning electron microscope (FE-SEM, trade name "JSM-6701FONO", supplied by JEOL). FIG. 3 demonstrates that peaks appear more intensely with an increasing PVP concentration, indicating that the degree of crystallinity of rutile titanium dioxide nanoparticles increases as depending on the PVP concentration. FIGS. 4 and 5 demonstrate that the exposed area of the novel exposed face (001) increases with an increasing PVP concentration, and along with this, the (111) face decreases in area.

The average particle sizes (d) of the $TiO_2$ samples were determined according to Scherrer Equation shown below.

Average particle size (d)=0.9λ/β cos θ wherein λ represents the wavelength of X-ray used; β represents the half-width of the diffraction profile; and 2θ represents the diffraction angle.

In addition, the specific surface areas of the samples were measured according to the Brunauer-Emmett-Teller method (BET method) using a nitrogen adsorption analyzer (trade name "Autosorb-1", supplied by Quantachrome Corporation). The results are collectively shown in following Table 1.

TABLE 1

| | Synthesis conditions | | | Average | BET specific |
|---|---|---|---|---|---|
| | $TiCl_3$ (M) | NaCl (M) | PVP (mM) | particle size (nm) | surface area ($m^2/g$) |
| MT-600B | — | — | — | 50 | 25-35 |
| SH5-0PVP | 0.15 | 5 | 0 | 58.66 | 21.84 |
| SH5-0.1PVP | 0.15 | 5 | 0.1 | 47.43 | 26.27 |
| SH5-0.25PVP | 0.15 | 5 | 0.25 | 51.68 | 27.89 |
| SH5-0.5PVP | 0.15 | 5 | 0.5 | 56.02 | 30.63 |

<Photocatalytic Activity Assessment>

The photocatalytic activities of the $TiO_2$ samples obtained in Examples 1 to 4 and Comparative Example 1 were assessed by oxidizing acetaldehyde or toluene in a gas phase using the samples and measuring evolved $CO_2$ levels.

A Tedlar bag (supplied by AS ONE Corporation) was used as a reactor. Each 100 g of the $TiO_2$ samples obtained in Examples 1 to 4 and Comparative Example 1 was spread over a glass dish, placed in the reactor, and 500-ppm acetaldehyde-saturated gas (or 100-ppm toluene-saturated gas) was blown into the reactor. After the gas and acetaldehyde (or toluene) achieved a state of equilibrium, photoirradiation was performed at room temperature (25° C.). A lighting system with a 500-W xenon lamp (trade name "SX-UI501XQ", supplied by Ushio Inc.) was used as a light source, and a UV-35 filter was used to cut off rays having wavelengths shorter than 350 nm. The quantity of light was controlled to 30 $mW/cm^2$ by using a fine stainless steel mesh as a light controlling filter.

Figure 6:
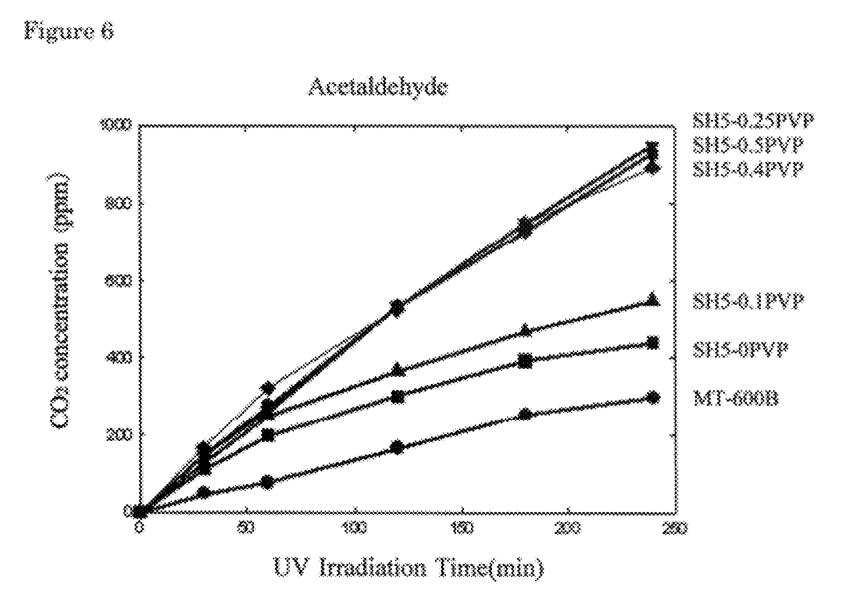
FIG. 6 is a graph illustrating how the $CO_2$ concentration ($CO_2$ consentration) varies depending on the ultraviolet ray irradiance (UV Irradiation Time), which $CO_2$ concentration is the concentration of $CO_2$ evolved upon oxidation of acetaldehyde using, as photocatalysts, a titanium dioxide (MT-600B) and the rutile titanium dioxides synthetically prepared at different PVP concentrations in the examples and comparative example.
Figure 7:
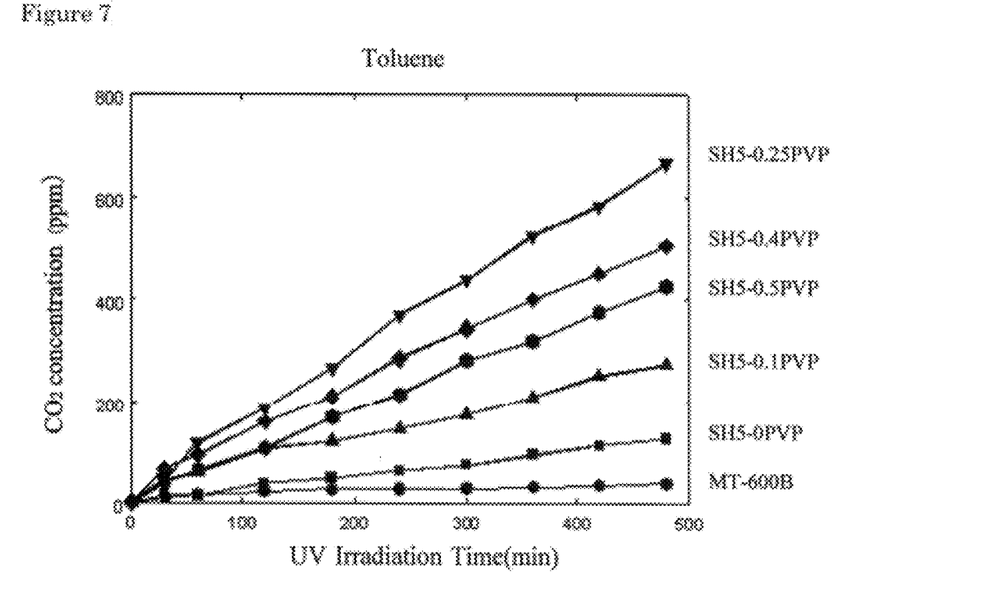
FIG. 7 is a graph illustrating how the $CO_2$ concentration ($CO_2$ consentration) varies depending on the ultraviolet ray irradiance (UV Irradiation Time), which $CO_2$ concentration is the concentration of $CO_2$ evolved upon oxidation of toluene using, as photocatalysts, the titanium dioxide (MT-600B) and the rutile titanium dioxides synthetically prepared at different PVP concentrations in the examples and comparative example.

After the initiation of photoirradiation, the quantities of evolved $CO_2$ were measured using a gas chromatograph (trade name "GC-8A", "GC-14A", supplied by Shimadzu Corporation) equipped with a hydrogen flame ionization detector attached with a methanizer (FIGS. 6 and 7).

The above description demonstrate that the exposed area of the novel exposed face (001) of $TiO_2$ particles varies depending on the PVP concentration; and that the photocatalytic activity of the $TiO_2$ varies depending not on the surface area dimensions such as specific surface area and crystal size but on the crystal surface structure. This is because excited electrons and holes are separated from each other and prevented from recombination, and this allows the $TiO_2$ particles to exhibit a strong catalytic activity. Specifically, the rutile titanium dioxide nanoparticles according to the present invention having the exposed crystal face (001) help to prevent the recombination of holes and excited electrons, because the holes are present in the (001) face, whereas the excited electrons are present in the (110) face, and this allows complete separation of the holes from the excited electrons. Thus, the rutile titanium dioxide nanoparticles can exhibit satisfactory photocatalytic activities and can exhibit satisfactory oxidizing, decomposing activities on organic compounds.

Industrial Applicability

The rutile titanium oxide nanoparticles according to the present invention can exhibit strong oxidizing actions and, when used as a photocatalyst, can efficiently oxidize organic substances. They are therefore useful for the purposes typically of air purification, deodorization, water purification, antimicrobe, and antifouling.

The invention claimed is:

1. A rutile titanium dioxide nanoparticle having exposed crystal faces (111), (110), and (001).

2. A method for producing rutile titanium dioxide nanoparticles, comprising the step of subjecting a titanium compound to a hydrothermal treatment in the presence of a hydrophilic polymer in an aqueous medium to yield rutile titanium oxide nanoparticles each having an exposed crystal faces (111), (110), and (001) according to claim 1.

3. The method for producing rutile titanium dioxide nanoparticles according to claim 2, wherein the hydrophilic polymer is a polyvinylpyrrolidone.

4. A photocatalyst comprising rutile titanium dioxide nanoparticles each having exposed crystal faces (111), (110), and (001) according to claim 1.

5. A method for oxidizing an organic compound, comprising the step of oxidizing an organic compound having an oxidizable moiety with molecular oxygen or a peroxide under photoirradiation in the presence of a photocatalyst including rutile titanium dioxide nanoparticles each having an exposed crystal faces (111), (110), and (001) according to claim 1.

6. The rutile titanium dioxide nanoparticle according to claim 1, wherein the rutile titanium dioxide nanoparticle has only the exposed crystal faces (111), (110), and (001).

* * * * *